US009025847B2

(12) United States Patent
Kitamura et al.

(10) Patent No.: US 9,025,847 B2
(45) Date of Patent: May 5, 2015

(54) IMAGE PROCESSING APPARATUS, CONTROL METHOD, AND OPTICAL COHERENCE TOMOGRAPHY SYSTEM

(75) Inventors: Takeshi Kitamura, Port Washington, NY (US); Makoto Sato, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 178 days.

(21) Appl. No.: 13/581,725

(22) PCT Filed: Feb. 24, 2011

(86) PCT No.: PCT/JP2011/001050
§ 371 (c)(1),
(2), (4) Date: Aug. 29, 2012

(87) PCT Pub. No.: WO2011/108231
PCT Pub. Date: Sep. 9, 2011

(65) Prior Publication Data
US 2012/0321166 A1    Dec. 20, 2012

(30) Foreign Application Priority Data

Mar. 2, 2010   (JP) .................. 2010-045544
Jan. 7, 2011   (JP) .................. 2011-002089

(51) Int. Cl.
| | | |
|---|---|---|
| G06K 9/00 | (2006.01) |
| A61B 3/12 | (2006.01) |
| A61B 3/00 | (2006.01) |
| A61B 3/10 | (2006.01) |
| A61B 6/00 | (2006.01) |

(52) U.S. Cl.
CPC .............. *A61B 3/1225* (2013.01); *A61B 3/0058* (2013.01); *A61B 3/102* (2013.01)

(58) Field of Classification Search
CPC ..................... G06K 9/00; A61B 1/00

USPC .............. 382/128–134; 378/4, 8, 21–27, 101, 378/901; 600/407, 410, 411, 425, 427; 128/920, 922
See application file for complete search history.

(56) References Cited

U.S. PATENT DOCUMENTS 7,864,331 B2 *  1/2011  Teramura et al. ............. 356/479
8,421,855 B2 *  4/2013  Buckland et al. .............. 348/78
(Continued)

FOREIGN PATENT DOCUMENTS

| CN | 001694644 A | 11/2005 |
| CN | 101268927 A | 9/2008 |
| EP | 1972271 A1 | 9/2008 |

(Continued)

OTHER PUBLICATIONS

Under the editorship of Mikio Takagi, et al. New Edition, Image Analysis Handbook. University of Tokyo Press.

*Primary Examiner* — Abolfazl Tabatabai
(74) *Attorney, Agent, or Firm* — Canon U.S.A.Inc., IP Division

(57) ABSTRACT

In an image processing apparatus, Whether image quality of a tomographic image corresponding to a predetermined position in an imaging target captured by an optical coherence tomography apparatus is within a predetermined range is determined, an instruction whether to permit the image capturing in the predetermined position is issued to the optical coherence tomography apparatus according to a determination that the image quality is out of the predetermined range, and a new tomographic image is generated by combining the tomographic image obtained according to the instruction and the tomographic image whose image quality is determined.

26 Claims, 14 Drawing Sheets

(56) References Cited

U.S. PATENT DOCUMENTS 8,696,123 B2 * 4/2014 Miyasa et al. ............... 351/206
2009/0268020 A1 10/2009 Buckland

FOREIGN PATENT DOCUMENTS

| | | |
|---|---|---|
| EP | 2130486 A1 | 12/2009 |
| EP | 2184006 A1 | 5/2010 |
| JP | H06-511312 A | 12/1994 |
| JP | H07-171142 A | 7/1995 |
| JP | 2008-237238 A | 10/2008 |
| KR | 100452645 A | 10/2004 |
| WO | 2004/002298 A1 | 1/2004 |
| WO | 2006/058735 A1 | 6/2006 |

* cited by examiner

-2.404　　　　　　　　　　　　　　　　　　　　　91.207
　Count:256000　　　Min:-2.404
　Mean:55.833　　　　Max:91.207
　StdDev:7.739　　　Mode:55.920 (6546)
　Bins:256　　　　　　Bin Width:0.366

0　　　　　　　　　　　　　　　　　　　　　　65535
　Count:256000　　　Min:0
　Mean:19760.301　　Max:65535
　StdDev:8633.019　Mode:14956 (7922)
　Bins:256　　　　　　Bin Width:255.996

IMAGE PROCESSING APPARATUS, CONTROL METHOD, AND OPTICAL COHERENCE TOMOGRAPHY SYSTEM

TECHNICAL FIELD

The present invention relates to an image processing apparatus that performs image processing of a tomographic image of a retina acquired by an optical coherence tomography apparatus, a control method of the optical coherence tomography apparatus, and an optical coherence tomography system.

BACKGROUND ART

In recent years, optical coherence tomography apparatuses using a principle of an optical coherence tomography (OCT) have been put into practical use. In the OCT, based on interference light of reflection or scattering light of measurement light entered at a predetermined position of a target of the imaging and reference light received via a reference object, a structure in the depth direction of the position where the measurement light entered is imaged. Using the principle, in the optical coherence tomography apparatus, a two-dimensional or three-dimensional tomographic image can be obtained by fixing an eye to be examined and scanning a retina by changing incident positions of the measurement light. By the processing, an internal structure of the target of the imaging can be observed.

In order to increase a signal-to-noise (S/N) ratio in the tomographic image acquired by the optical coherence tomography apparatus, a technique for performing addition-average processing to a plurality of images and generating a tomographic image having good image quality has been provided. For example, Patent Document 1 discusses a technique for combining a plurality of tomographic images of a retina captured in advance and generating a high-quality still image.

CITATION LIST

Patent Literature

PTL 1: Japanese Patent Application Laid-Open No. 2008-237238

Non Patent Literature

Under the editorship of Mikio Takagi, et al. New Edition, Image Analysis Handbook. University of Tokyo Press.

SUMMARY OF INVENTION

Technical Problem

In capturing images of a retina of a subject's eye, the subject's eye is fixed by using a fixation lamp. Accordingly, it is preferable to shorten the image capturing time to reduce the burden in the imaging. However, in the technique discussed in the Patent Document 1, from the tomographic images captured in advance, the tomographic images are selected and combined. Accordingly, unnecessary imaging may have been performed for the image quality to be obtained.

Solution to Problem

According to an aspect of the present invention, an image processing apparatus is provided. The image processing apparatus includes a determination unit configured to determine whether image quality of a tomographic image corresponding to a predetermined position in an imaging target captured by an optical coherence tomography apparatus is within a predetermined range, a control unit configured to perform control whether to permit the image capturing in the predetermined position to the optical coherence tomography apparatus in response to a determination that the image quality is out of the predetermined range by the determination unit, and a generation unit configured to generate a new tomographic image by combining the tomographic images in the predetermined position including the tomographic images obtained according to the control.

ADVANTAGEOUS EFFECTS OF INVENTION

According to the present invention having such structure, according to image quality, an image capturing instruction is issued as needed, the captured images are combined, and a new tomographic image is generated. Accordingly, unnecessary burden of the subject can be reduced and images of desired image quality can be obtained.

Further features and aspects of the present invention will become apparent from the following detailed description of exemplary embodiments with reference to the attached drawings.

BRIEF DESCRIPTION OF DRAWINGS

The accompanying drawings, which are incorporated in and constitute a part of the specification, illustrate exemplary embodiments, features, and aspects of the invention and, together with the description, serve to explain the principles of the invention.

DESCRIPTION OF EMBODIMENTS

Various exemplary embodiments, features, and aspects of the invention will be described in detail below with reference to the drawings. Hereinafter, the exemplary embodiments of the present invention will be described with reference to the attached drawings.

EXAMPLE 1

Figure 1:
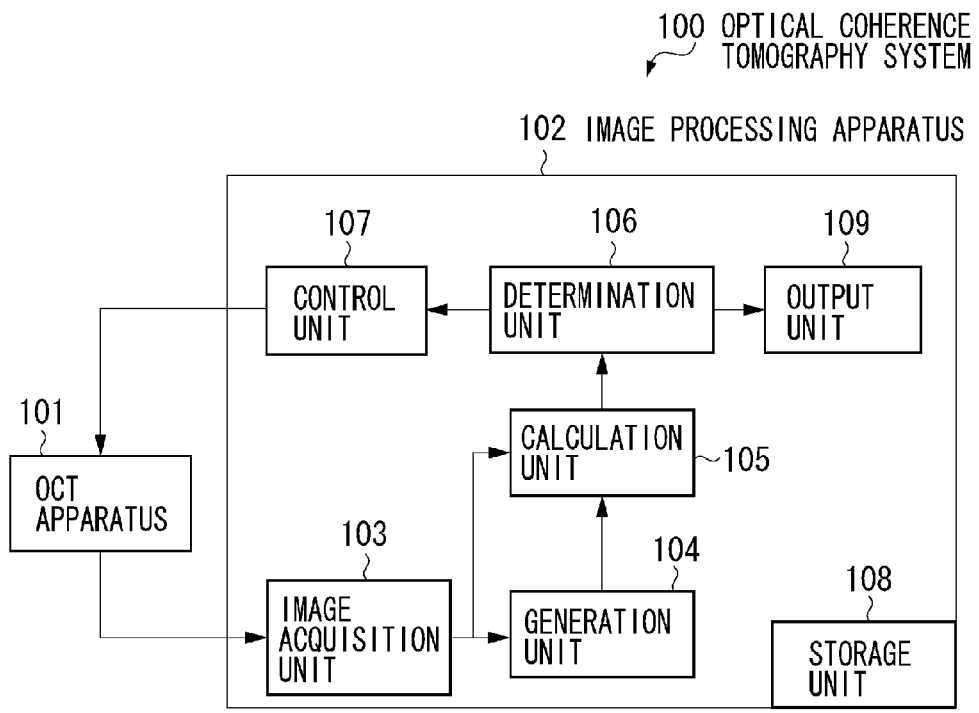
FIG. 1 is a block diagram illustrating a configuration of an optical coherence tomography system 100.

The configuration of an optical coherence tomography system according to an exemplary embodiment of the present invention is described with reference to FIG. 1. An optical coherence tomography system 100 includes an optical coherence tomography apparatus (hereinafter, referred to as OCT apparatus 101) that captures a tomographic image of an imaging target and an image processing apparatus 102 that performs addition processing of the images captured by the OCT apparatus 101 and issuing imaging instructions. The OCT apparatus 101 and the image processing apparatus 102 are connected with each other.

The image processing apparatus 102 includes an image acquisition unit 103 that acquires an image from the OCT apparatus 101, a generation unit 104 that generates a combined image from tomographic images, a calculation unit 105 that calculates a value indicating image quality of an image, a determination unit 106, a control unit 107 that controls whether to permit recapturing an image, a storage unit 108, and an output unit 109. The image processing apparatus 102 is, for example, an electronic computer, and has dedicated internal circuits corresponding to each of the above-described units.

The image acquisition unit 103 is communicably connected to the OCT apparatus 101. The image acquisition unit 103 acquires a tomographic image of the imaging target captured by the OCT apparatus 101. The tomographic image acquired by the image acquisition unit 103 is, in the present exemplary embodiment, a two-dimensional tomographic image obtained by scanning between predetermined two positions on the surface of a retina.

The generation unit 104 generates a new tomographic image based on original data of the tomographic image captured by the image acquisition unit 103 and a combined image that has already been generated by the generation unit 104 by aligning the images, performing addition-average processing on each pixel, and combining the images. Through the processing, a tomographic image whose random noise is reduced can be obtained. The tomographic images to be the target of the combination by the generation unit 104 are tomographic images corresponding to predetermined positions of the imaging target.

Due to involuntary eye movement and limitations of the apparatus, tomographic images strictly combined at the same position may not be obtained. However, the generation unit 104 performs the processing of combining the plurality of tomographic images acquired by the imaging apparatus on the premise that the OCT apparatus 101 has captured the tomographic images at the same position. If an amount of deviation due to the involuntary eye movement or the like can be estimated, a tomographic image corrected by the amount of deviation can be used. The generated image is stored in an internal memory and used for generation of a combined image next time. The generation unit 104 is described in detail below.

The calculation unit 105 analyzes the captured tomographic images and the combined image generated by the generation unit 104, and calculates values indicating the quality of the images. For the values indicating the image quality, an S/N ratio, or the like can be employed. The calculated values are stored in the storage unit 108. When a first tomographic image is transmitted from the OCT apparatus 101, the calculation unit 105 calculates the value indicating the image quality of the tomographic image, and inputs the value indicating the image quality into the determination unit 106.

When a second tomographic image or a tomographic image after the second tomographic image is input, the calculation unit 105 calculates a value indicating the image quality of the tomographic image combined by the generation unit 104. For example, the calculation unit 105 calculates an S/N ratio from the combined tomographic image according to the following mathematical expression (1), and outputs as an image quality index M.

$$M = S/N \qquad \text{mathematical expression (1)}$$

In the mathematical expression, S is a value indicating the strength of a signal component in the image. The value can be any numerical value as long as the strength of the signal component representing the subject is indicated such as a maximum value, a difference between the maximum value and a minimum value, or a difference between average values in two different regions of pixels contained in an overlapped B-scan image. N is a value indicating the strength of a noise component. The N can be a standard deviation or a root-mean-square in a region the subject is not imaged.

If the imaging target is a retina of a human's eye, it is preferable to select regions to be used for diagnosis, for example, a combination of a nerve fiber layer and a ganglion cell layer. Such regions can be automatically set by an image index calculation unit 3 by analyzing the overlapped B-scan image. Alternatively, regions whose existence possibility of a desired layer is high can be set in advance at the time of adjusting the apparatus.

The determination unit 106 determines whether the value indicating the image quality of the tomographic image acquired by the image acquisition unit 103 or the tomographic image generated by the generation unit 104 is within a predetermined range. The predetermined range is, for example, a value indicating a range of image quality necessary for the image used for diagnosis.

If the determined value indicating the image quality is within the predetermined range, it is determined that the image quality satisfies the standard. The output unit 109 outputs the image of the image quality. If the value is out of the predetermined range, it is determined that the image quality of the image does not satisfy the standard. Then, information indicating that the standard of the image quality of the image is not satisfied is input into the control unit 107. The information that indicates the predetermined range of the image quality is stored in the storage unit 108, and is referred to by the determination unit 106 as needed.

The control unit 107 controls whether to permit the OCT apparatus 101 to perform image capturing based on the determination result. If the determination unit 106 determines that the image quality does not satisfy the necessary standard, the control unit 107 transmits instruction information for capturing an image of the same position as the predetermined position captured in the tomographic image to the OCT apparatus 101.

In response to the instruction, the OCT apparatus 101 re-captures the image of the retina of the subject's eye, and transmits the tomographic image of the specified part to the image processing apparatus 102. If the determination unit 106 determines that the image quality is within the predetermined range, the control unit 107 transmits a signal not to permit image capturing to the OCT apparatus 101.

The storage unit 108 stores the value indicating the range to be the standard for the image quality. For example, the value is a predetermined threshold with respect to the value indicating the image quality; if a value is equal to or greater than the threshold, the standard of the image quality is satisfied, and if the value is less than the threshold, the standard is not satisfied. The value indicating the range can be determined in advance or defined according to the input by a user. The output unit 109 outputs the received tomographic image to a display unit (not illustrated) or a printer (not illustrated).

By the processing, if the image quality of the captured tomographic image does not satisfy the standard, an instruction for re-capturing an image of the same region can be issued, and the captured image is combined. Accordingly, a tomographic image having the reduced noise can be obtained. Moreover, the image quality is calculated as needed and whether the standard is satisfied is determined. Accordingly, unnecessary imaging is not performed, and burden of the subject in the imaging can be reduced.

Figure 2:
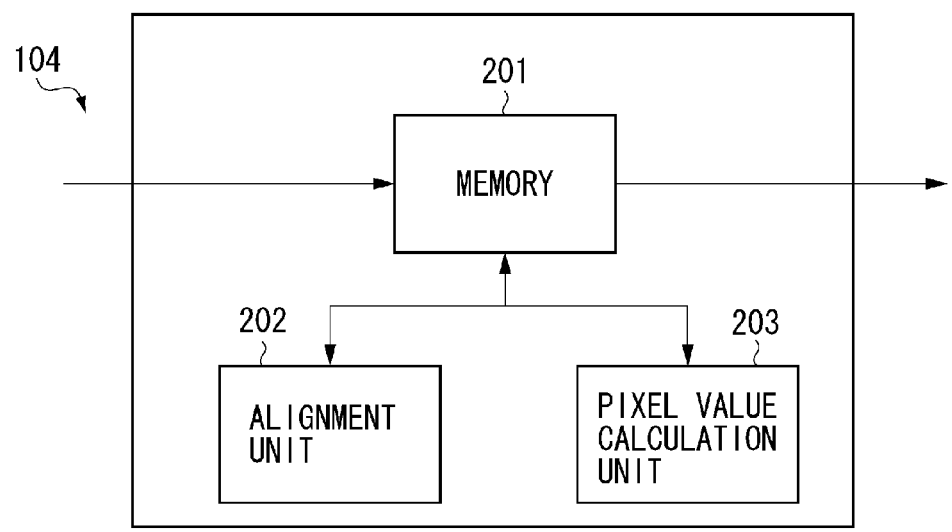
FIG. 2 is a block diagram illustrating a configuration of a generation unit 104.

Now, the generation unit 104 is described in detail with reference to FIG. 2. The generation unit 104 includes a memory 201, the alignment unit 202, and a pixel value calculation unit 203. The memory 201 stores the tomographic images captured by the image acquisition unit 103 and the combined tomographic image stored in the storage unit 108. The tomographic images correspond to the same position of the retina of the same person.

The alignment unit 202 sequentially performs alignment of the tomographic images to be combined that are stored in the memory 201. Then, the alignment unit 202 calculates values of new pixels from the pixels corresponding to the same position of the subject, generates an overlapped B-scan image, and outputs it. The alignment processing is processing for determining a relative position relationship having the highest matching rate with respect to a plurality of images.

Even if tomographic images for the same position are captured, due to deviation of the images caused by involuntary eye movement or the like, the positions may not be strictly matched. Thus, by calculating positions of the pixels having the highest similarity, a corresponding coordinate value can be calculated.

For the method for calculating the coordinate value, a known method for aligning images can be employed. For example, the template matching method described in the Non-patent Literature 1 can be employed.

The pixel value calculation unit 203 performs addition-average processing on the values of the new pixels from the pixels corresponding to the same position of the subject, generates a combined tomographic image, and outputs it. In the exemplary embodiments of the present invention, the addition-average processing includes not only a simple arithmetic average, but also includes weighted average for performing weighting on each image and calculating an average. The combining processing performed by the pixel value calculation unit 203 is described with reference to FIG. 3.

Figure 3:
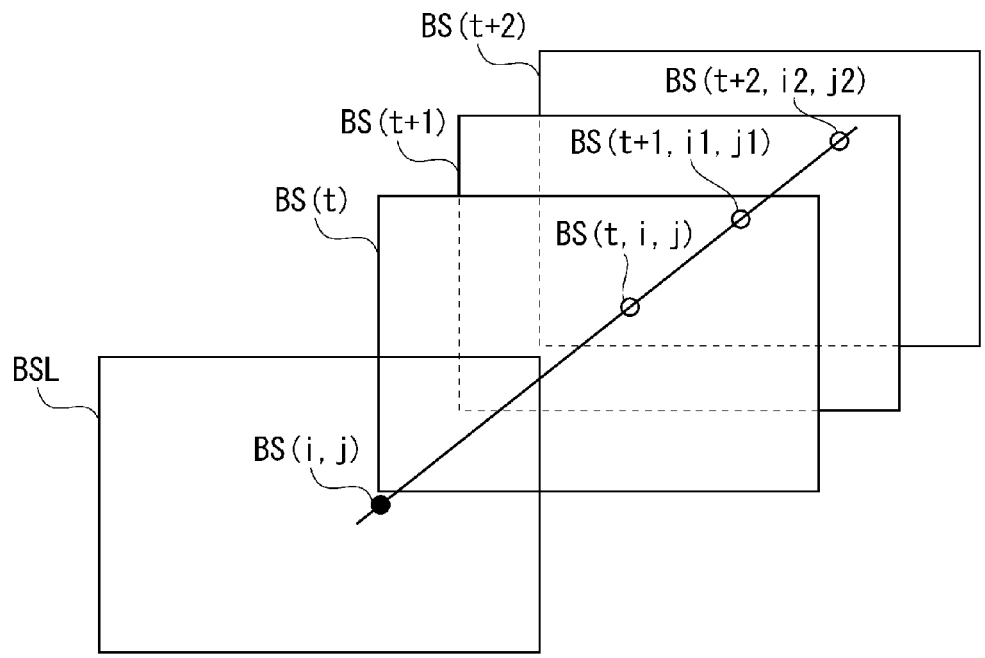
FIG. 3 illustrates processing of addition-average performed on an image by the generation unit 104.
Figure 3:
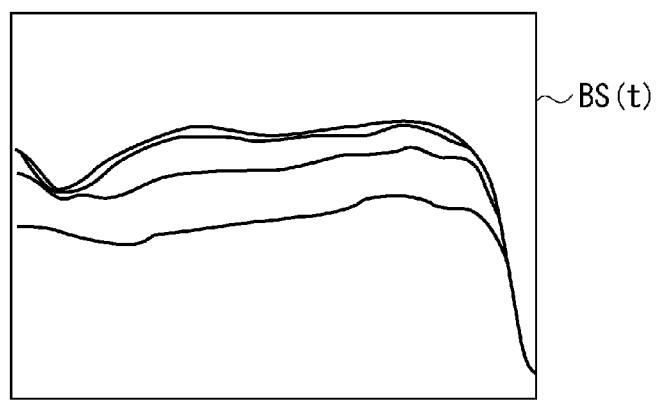

FIG. 3 illustrates overlapping processing performed when three tomographic images from t–th to t+2th are stored in the memory 201. Tomographic images to be combined are expressed as BS(t), BS(t+1), and BS(t+2). A combined image is expressed as BSL.

In the combined tomographic image BSL, a pixel value BSL (i, j) of a position (i, j) is calculated from pixels BS (t, i, j), BS (t+1, i1, j1), and BS (t+2, i2, j2) corresponding to the same position of the subject in each tomographic image BS (t) according to the following mathematical expression (2). In the mathematical expression, only the BS (t) is a tomographic image obtained by combining n-sheets of the tomographic images. The BS (t+1) and the BS (t+2) are formed by the imaging apparatus, and acquired by the image acquisition unit 103.

$$BSL(i,j)=(N*BS(t,i,j)+BS(t+1,i1,j1)+BS(t+2,i2,j2))/(N+2),$$ mathematical expression (2)

wherein, i, i1, and i2, and j, j1, and j2 are coordinate values in a horizontal direction and a vertical direction corresponding to the same part of the subject created in each tomographic image.

The combined tomographic image is stored in the memory 201, and the image is also transmitted to the storage unit 108 and stored. By updating the combined tomographic image BSL by always storing the combined tomographic image in the memory 201, a necessary capacity of the memory 201 can be reduced. In such a case, in order to shorten the overall processing time, it is preferable to simultaneously perform the acquisition of the newly captured tomographic image and the combining processing.

On the pixel of the overlapped B-scan image BSL, it is not always necessary to perform the averaging processing illustrated in the mathematical expression 2. A median value discussed in the Patent Document 1 can be used or weighted averaging processing can be performed. For example, from a plurality of images that are aligned in the alignment processing unit, an image to be a reference can be set, and a position of each pixel in the image can be set as a reference position. As the amount of deviation of an image or pixels to the reference position is large, the weighting can be reduced and the addition-average processing can be performed.

By the processing, the effect by the image that is largely deviated from the reference image on the combined image is reduced. Accordingly, a blur of the edge of the image can be reduced. The above-described storage method of the B-scan and calculation methods of the pixels of the overlapped B-scan image can be modified and applied without departing from the scope of the invention.

Figure 4:
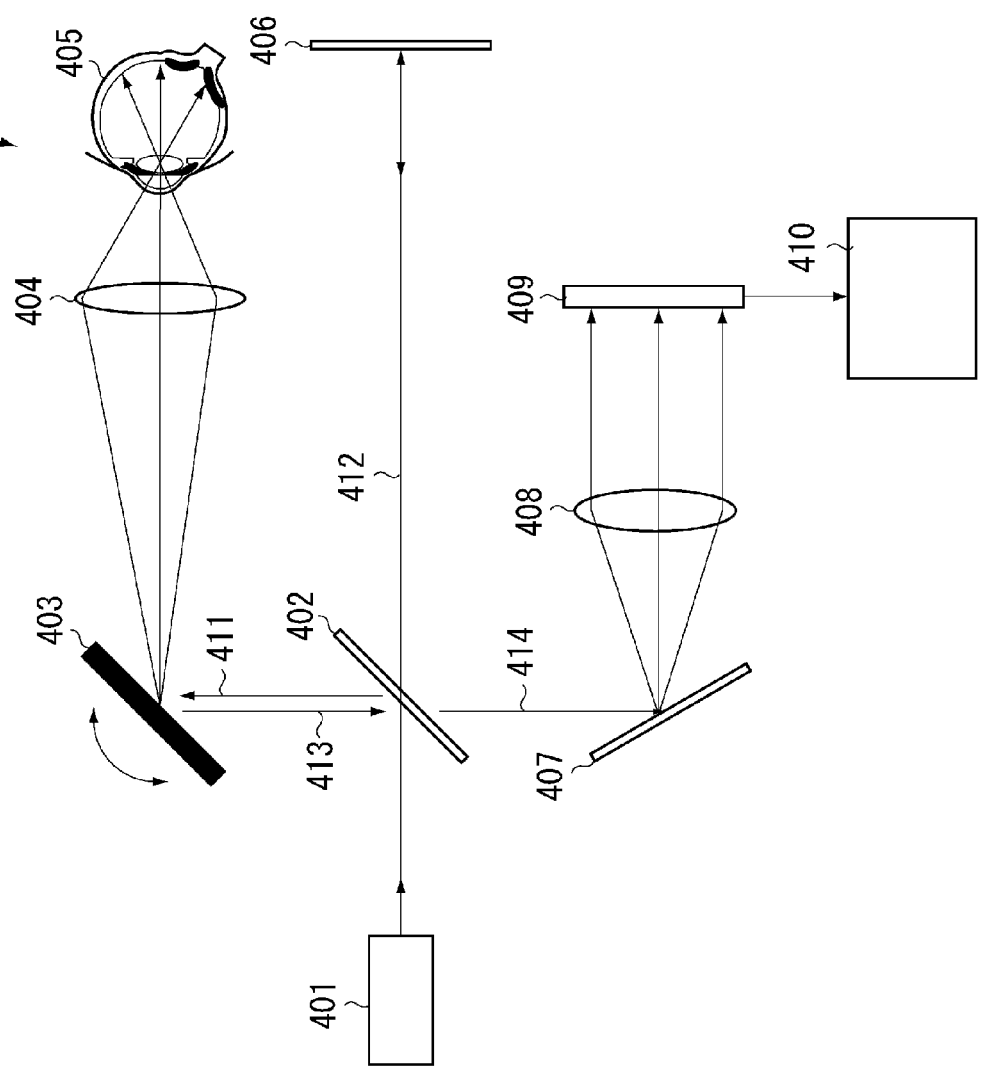
FIG. 4 illustrates a configuration of an OCT apparatus 101.

Next, the configuration of the OCT apparatus 101 is described in detail with reference to FIG. 4. The OCT apparatus 101 according to the present exemplary embodiment is a so-called Fourier domain optical coherence tomography apparatus. The OCT apparatus 101 performs image capturing of a subject's eye according to the operation information input in an operation unit (not illustrated) by an operator, and transmits the acquired image to the image processing apparatus 102.

A light source 114 emits light. A beam splitter 115 splits the light into measurement light 124 and reference light 125. The measurement light 124 passes through an eye 118 that is the target of the observation and returns as returned light 126. The returned light 126 includes reflected light and scattering light of the measurement light on the eye 118.

The beam splitter 115 also serves as an interference light generation unit that mixes the returned light 126 and the reference light 125, and generates interference light 127. A diffraction grating 120 splits the interference light, and an image is formed on a one-dimensional sensor 122 by a lens 121.

Each pixel circuit in the one-dimensional sensor 122 outputs an electric signal corresponding to the amount of the received light. An image formation unit 123 performs Fourier transformation with the position in the one-dimensional sensor, that is, a wave number of the interference light, and acquires a tomographic image of the eye 118. The beam splitter can be an optical fiber coupler, or the like.

Next, the light source 114 is described in detail. The light source 114 is a super luminance diode (SLD) that is a typical low coherent light source. Its wavelength is 830 nm, and the bandwidth is 50 nm. The bandwidth has an effect on the resolution in the optical axis direction of the acquired tomographic image; accordingly, an important parameter.

As the light source, in the present exemplary embodiment, the SLD is selected. However, any light source can be employed as long as low coherent light can be emitted, and for example, amplified spontaneous emission (ASE) can be employed. With respect to the wavelength, because an eye is the target of the measurement, infrared light is preferable. Moreover, since the wavelength has an effect on the resolution in the horizontal direction of the acquired tomographic image, it is preferable to employ a short wavelength as much as possible. In the exemplary embodiment, a wavelength of 830 nm is employed. Depending on a measurement part of the observation target, the other wavelengths can be used.

Next, the optical path of the reference light 125 is described. The reference light 125 split by the beam splitter 115 is reflected by a mirror 119 that is a reference object, and returns to the beam splitter 115. By setting the optical path length to the same length as that of the measurement light 124, the reference light and the measurement light can interfere with each other.

Next, the optical path of the measurement light 124 is described. The measurement light 124 split by the beam splitter 115 enters the minor of an XY scanner 116. The XY scanner serves as a scanning optical system that performs raster scanning on the retina of the eye 118 two-dimensionally in a direction perpendicular to the optical axis by turning the incident measurement light 124 to the eye 118 and sequentially changing the direction.

For the sake of simplicity, the XY scanner 116 is described as one mirror. However, in reality, two minors of an X scan minor and a Y scan minor are closely arranged. The center of the measurement light 124 is adjusted so that the center corresponds to the rotation center of the minor of the XY scanner 116.

The lens 117 condenses the measurement light 124 on the retina. By the above-described optical system, if the measurement light 124 enters the eye 118, due to the reflection and scattering from the retina of the eye 118, becomes the returned light 126. The generation of the one-dimensional image by entering the measurement light at a position on the retina is referred to as A-scan. The one-dimensional image is referred to as an A-scan image.

The operation of performing the A-scan along a predetermined line on the surface of the retina at predetermined intervals and generating a two-dimensional image is referred to as B-scan. The two-dimensional image is referred to as a B-scan image. By the B-scan, a plurality of A-scan images at each incident position of the measurement light sequentially changed at the predetermined intervals can be obtained. By performing interpolation processing, and the like on the A-scan images, the two-dimensional B-scan image can be obtained.

Normally, in order to monitor the imaging position, the OCT apparatus includes a scanning laser ophthalmoscope (not illustrated) or an optical system for capturing a two-dimensional fundus image.

Next, the spectroscopic system is described. As described above, the interference light 127 is split by the diffraction grating 120. The light splitting is performed under the same wavelength conditions as the central wavelength and bandwidth of the light source. The one-dimensional sensor for measuring interference light generally has a charge-coupled device (CCD) type and a complementary metal-oxide semiconductor (CMOS) type. Either the CCD type or the CMOS type can provide similar results.

Figure 5A:
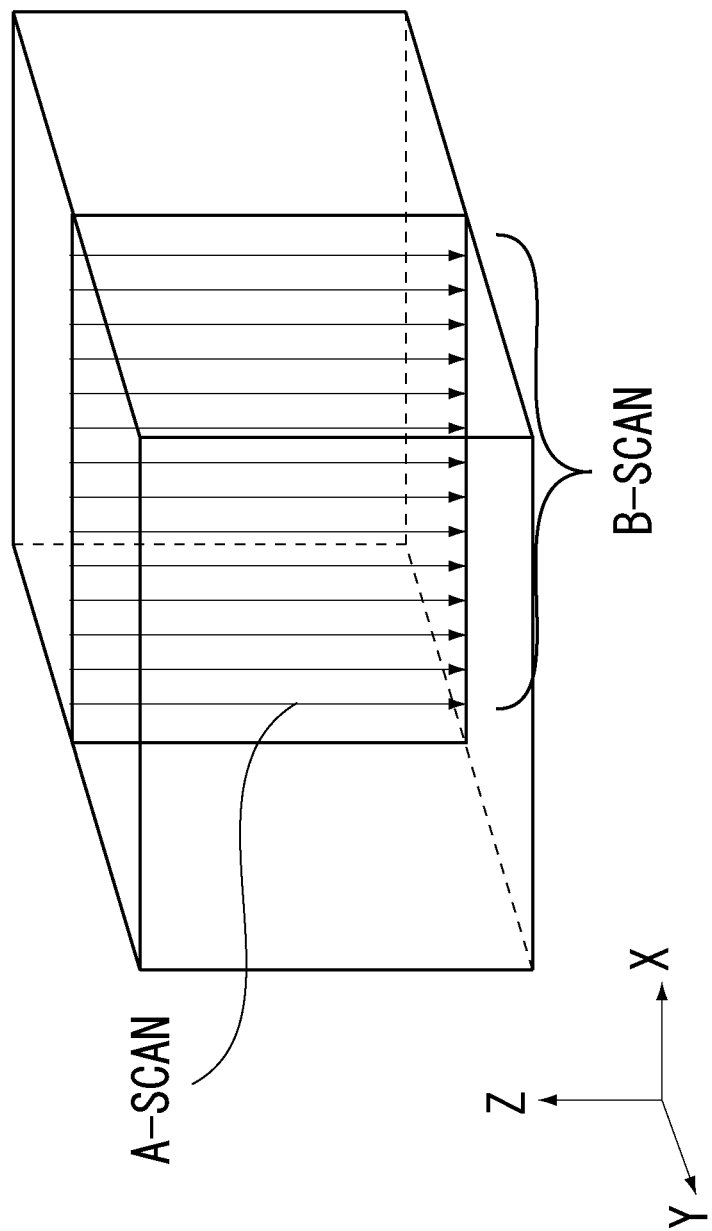
FIG. 5A illustrates A-scanning and B-scanning performed by the OCT apparatus.

In the above-described OCT apparatus 101, if measurement is performed without moving the XY scanner 403, from output of the Fourier transformation, the A-scan in FIG. 5A can be obtained. By continuing moving the scanner in the X direction by the amount of resolution for every A-scan completion, the B-scan in FIG. 5A can be obtained. Similarly, by continuing the scanning in the Y direction for every B-scan completion, a three-dimensional image of the retina can be obtained.

Figure 5B:
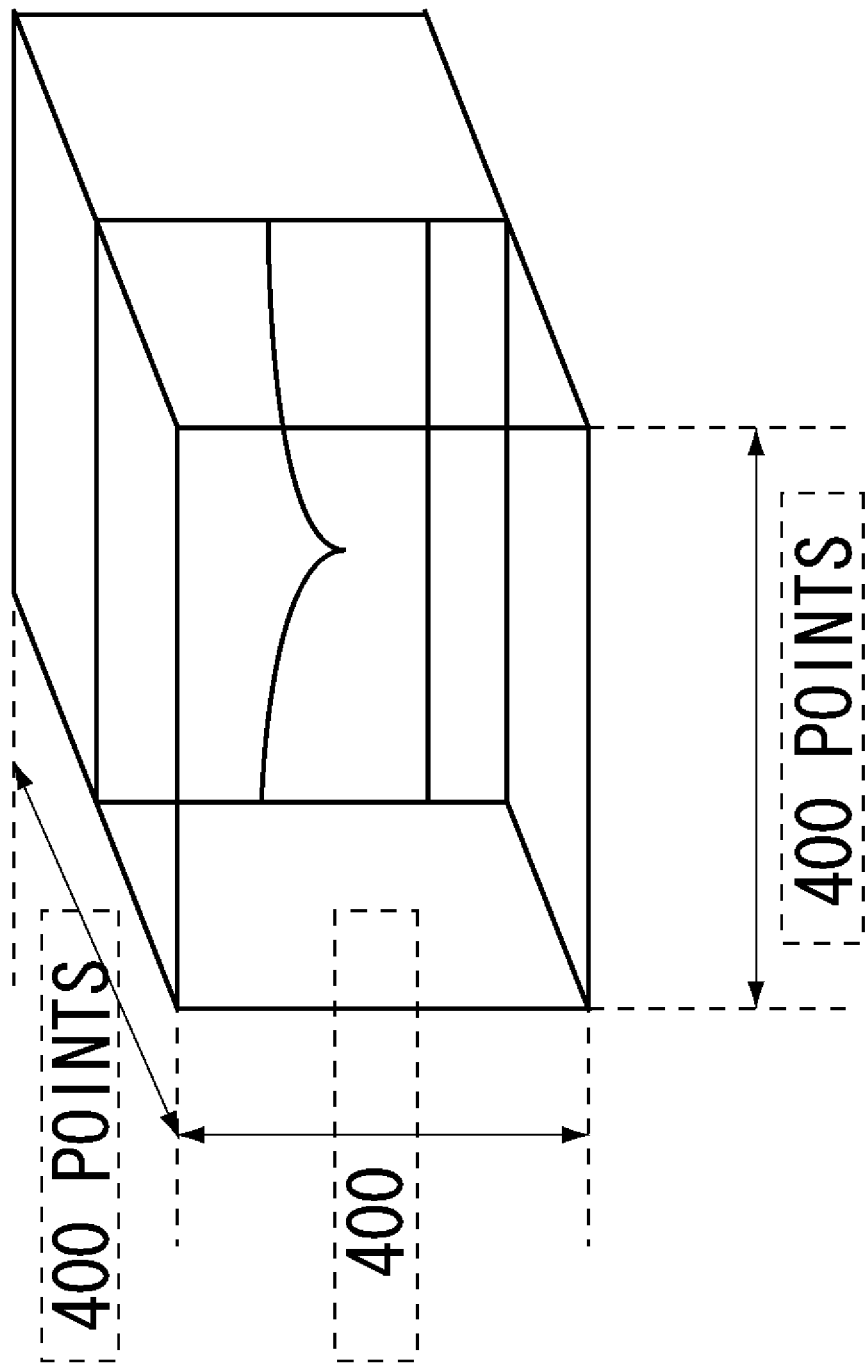
FIG. 5B illustrates A-scanning and B-scanning performed by the OCT apparatus.
Figure 5C:
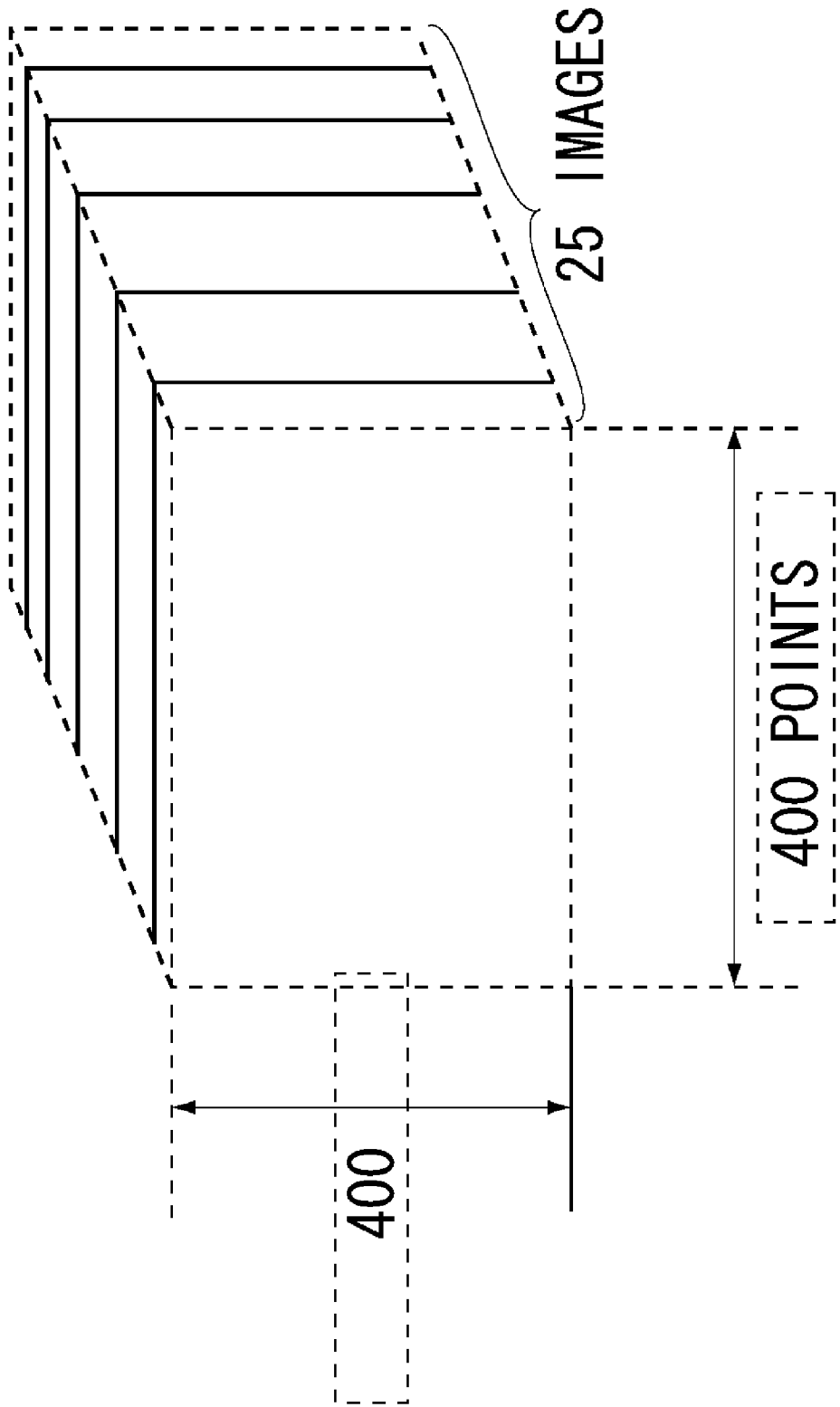
FIG. 5C illustrates A-scanning and B-scanning performed by the OCT apparatus.

In the operation, if the amount of shift of the scanning in the Y direction is small, a fine three-dimensional image like the image illustrated in FIG. 5B can be obtained. If the amount of shift of the scanning in the Y direction is large, a rough three-dimensional image (hereinafter, referred to as rough three-dimensional image) like the image illustrated in FIG. 5C can be obtained.

Figure 6:
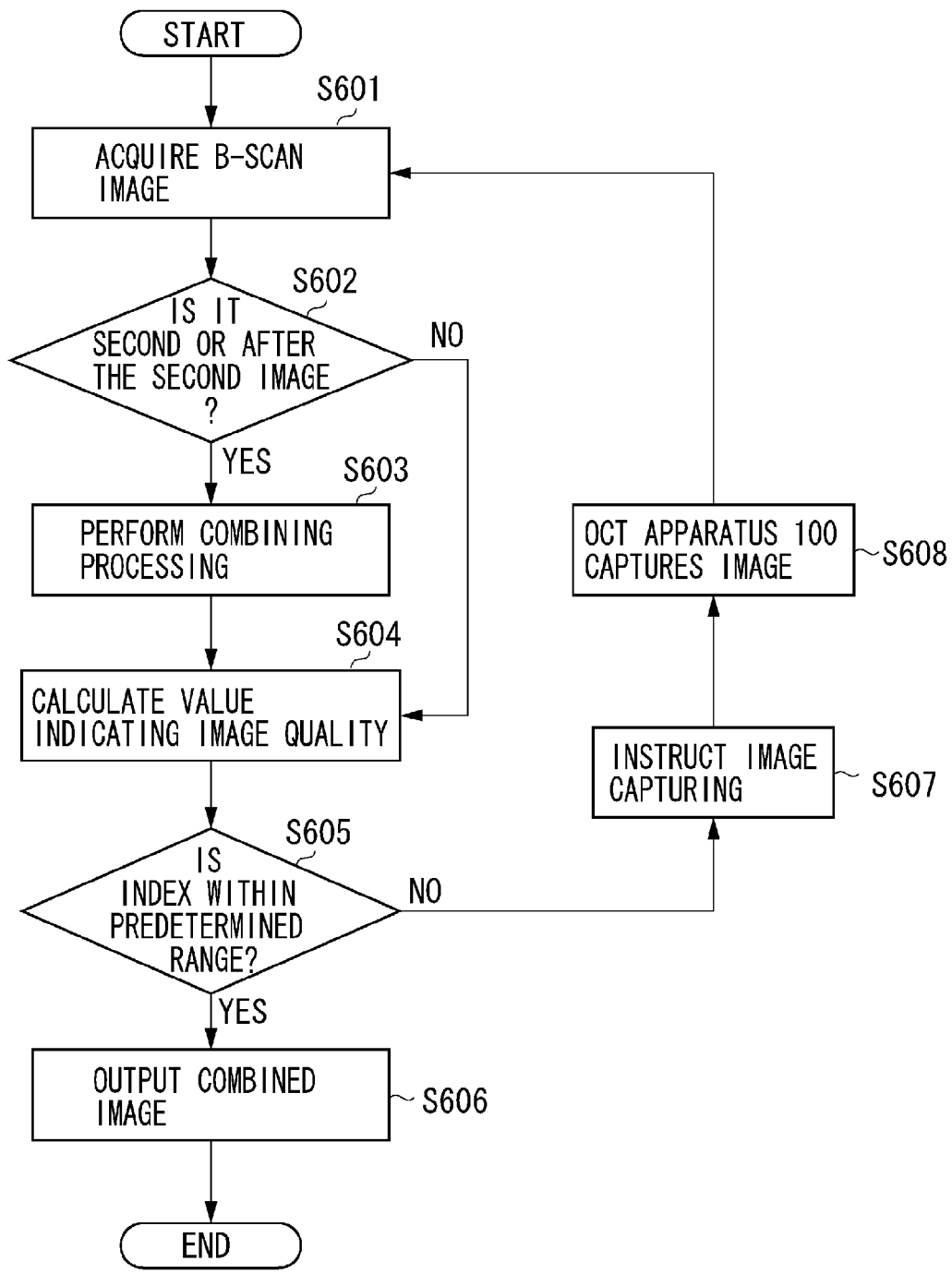
FIG. 6 is a flowchart illustrating the flow of processing performed by an image processing apparatus 102.

The flow of the image processing apparatus 102 according to the first exemplary embodiment is described with reference to the flowchart in FIG. 6.

In step S601, the image acquisition unit 103 acquires one B-scan image at a predetermined position in a subject's eye, like the above-described image illustrated in FIG. 3. The image acquisition unit 103 acquires a plurality of tomographic images formed by the OCT apparatus by scanning a predetermined two-dimensional imaging region. From the tomographic images, the B-scan image at the predetermined position is obtained. The other B-scan images are stored in the storage unit 108.

In step S602, if the above-mentioned B-scan image at the predetermined position is a first image (NO in step S602), there are not a plurality of images to be combined by the generation unit 104. Then, the image acquisition unit 103 transmits the acquired B-scan image to the calculation unit 105. In addition, the image acquisition unit 103 can transmit the B-scan image to the generation unit 104, and the generation unit 104 can transmit the B-scan image to the calculation unit 105 without performing any processing on the B-scan image. If the B-scan image is a second image or after the second image (YES in step S602), the image acquisition unit 103 transmits the B-scan image to the generation unit 104.

In step S603, the generation unit 104 stores the input B-scan image in the internal memory 201. In the memory 201 in the generation unit 104, the combined B-scan image that has already been generated is stored. Then, processing to combine the combined image and the newly input B-scan image is performed.

As described above, the generation unit 104 sequentially performs alignment of the B-scan images stored in the memory 201. Then, the generation unit 104 calculates values of new pixels from the pixels corresponding to the same positions of the subject, generates an overlapped B-scan image, and outputs it. The B-scan image already generated is updated by the generated B-scan image, and the image is stored in the memory 201.

The stored combined B-scan image is to be combined by the generation unit 104 when a next new B-scan image is input. The generation unit 104 outputs the image to the calculation unit 105.

In step S604, the calculation unit 105 calculates an index value M indicating the image quality of the B-scan image output from the image acquisition unit 103 or the generation unit 104.

In step S605, the determination unit 106 determines whether the input image quality index M exceeds a predetermined range. If the determination unit 106 determines that the index M is within the predetermined range (YES in step S605), the output unit 109 outputs the image that is determined to be the image whose image quality is within the predetermined range stored in the memory 201 in the generation unit 104, and displays the image on a display unit (not illustrated).

If the determination unit 106 determines that the index M is out of the predetermined range (NO in step S605), in step S607, the control unit 107 receives information about the determination, and instructs the OCT apparatus 101 to perform the image capturing again. In response to the instruction, the OCT apparatus 101 captures an image of the retina of the subject's eye.

In step S601, the image acquisition unit 103 acquires the above-described B-scan image in the predetermined position. In step S603, the generation unit 104 combines the tomographic image obtained according to the retake instruction by the control unit 107 with the tomographic image whose image quality is determined by the determination unit 106.

By the processing, the tomographic images in the predetermined position are sequentially combined. Then, a control unit (not illustrated) determines the number of sheets of the tomographic images necessary for obtaining a combined image having the image quality satisfying the standard for diagnosis. To the other B-scan images, the generation unit 104 performs the processing of combining tomographic images of the same number of sheets, and a plurality of B-scan images for clarifying a three-dimensional structure of the retina can be obtained.

The processing of performing the determination of the image quality and issuing the image capturing instruction corresponding to the determination as needed is effective especially in a case where the processing of generating the combined image and the calculation processing of the value indicating the image quality is sufficiently faster than the processing of scanning the imaging region of the retina and forming the image.

As described above, if the image quality index is out of the predetermined range, the recapturing of an image is instructed to generate the combined image, and when the image quality becomes within the predetermined range, the instruction of the recapturing an image is stopped. The combined B-scan image at the time is output by the output unit 109 from the memory 201 in the generation unit 104.

By the processing, unnecessary imaging is prevented, and the high-quality tomographic image can be obtained while the burden of the subject is reduced. Especially, depending on subjects, images of retinas captured by the OCT apparatus have different amounts of noise due to effects of involuntary eye movement, a vitreum, a crystalline lens in the measurement optical path, and the like. However, as compared to a case where the number of images to be combined is uniformly determined, more appropriate number of shots can be determined. Accordingly, both of the reduction of the burden of the subjects and the increase of the image quality can be achieved.

In the present exemplary embodiment, the first tomographic image is used in the processing of generating the combined image by the generation unit 104. However, in another exemplary example, the first tomographic image is not used in the generation of the combined image. For example, if a main image capturing is performed after pre-scan imaging for alignment in the image capturing is performed, the image processing apparatus 102 acquires the tomographic image obtained by the pre-scan imaging, and calculates an image quality evaluation value.

In the processing, the image quality of the main image capturing in the imaging region that is contained in the pre-scan image is determined. With respect to the tomographic image used only for the evaluation of the image quality, the image quality of the overall imaging region in the main image capturing is not always to be evaluated, but the image quality at a representative position is to be evaluated. By performing the above-described control, using the tomographic image of the pre-scan imaging, the appropriate overlapped image can be effectively obtained.

EXAMPLE 2

In the optical coherence tomography system 700 according to a second exemplary embodiment, an OCT apparatus 701 repeatedly captures images of a retina of a subject's eye, and an image acquisition unit 703 sequentially acquires the repeatedly formed tomographic images. A generation unit 705 sequentially generates and updates combined images. At the time the image quality becomes within a predetermined range, a control unit 708 issues an instruction for stopping the image capturing to the OCT apparatus 701. The OCT apparatus 701 repeats the image capturing in response to the instruction from the control unit 708 in advance. However, the OCT apparatus 701 can repeat the image capturing without the instruction from the control unit 708.

Figure 7:
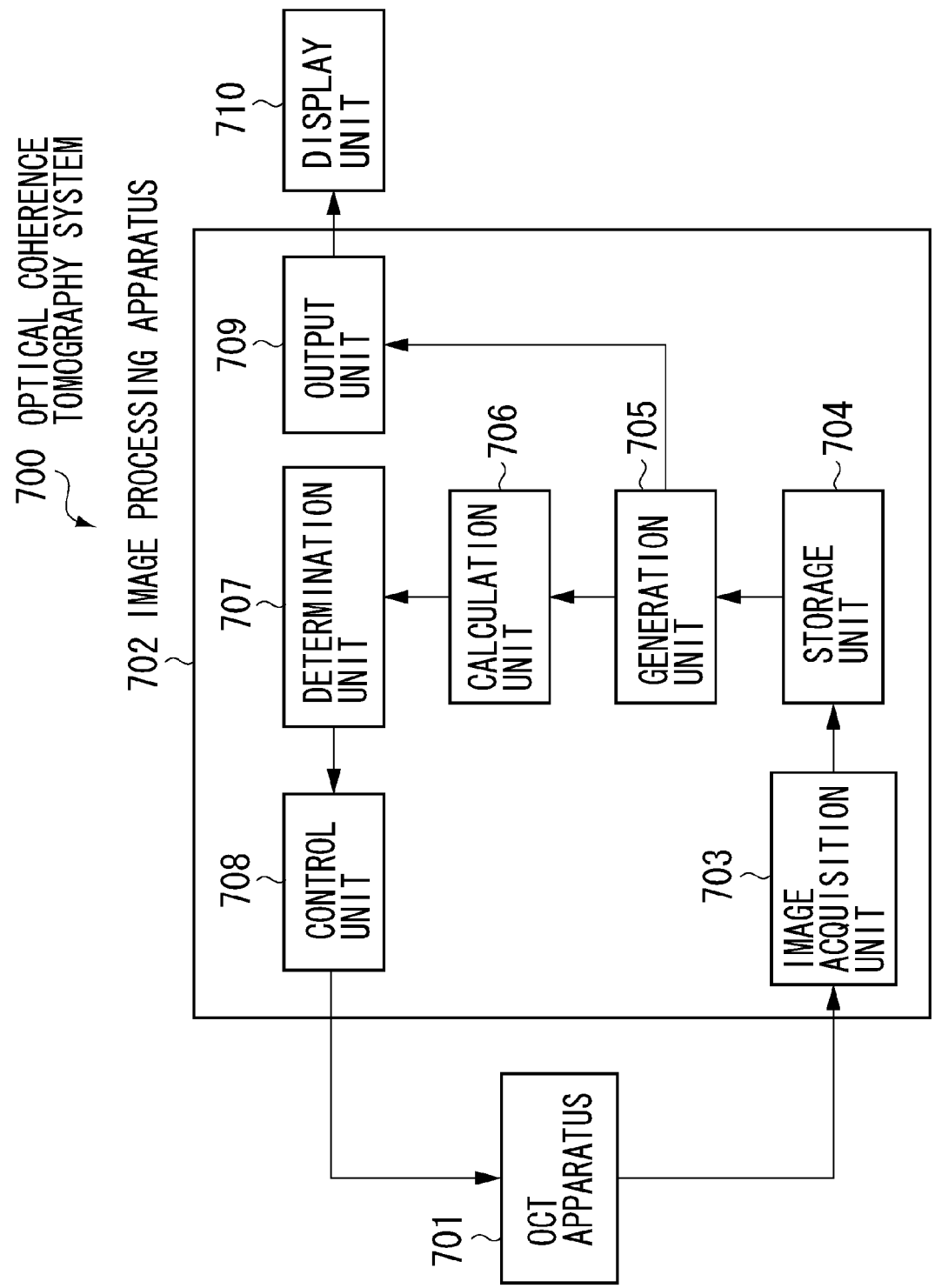
FIG. 7 is a block diagram illustrating a configuration of an optical coherence tomography system 700.

Hereinafter, the structure of the optical coherence tomography system 700 is described with reference to FIG. 7. With respect to components having the same names as those in the first exemplary embodiment, if not otherwise mentioned, similar functions are provided, and overlapping descriptions are omitted.

The OCT apparatus 701 is a so-called Fourier domain optical coherence tomography apparatus, like that in the first exemplary embodiment. However, the OCT apparatus 701 is different in that the OCT apparatus 701 repeatedly captures images of a retina to sequentially form tomographic images according to an image capturing instruction from the image processing apparatus 702.

The image acquisition unit 703 sequentially acquires the tomographic images captured in the OCT apparatus 701 corresponding to formation of the image. The image acquisition unit 703 transmits the acquired images to a storage unit 704, and instructs the storage unit 704 to store the image.

A generation unit 705 sequentially acquires the images from the storage unit 704 simultaneously with the image capturing by the OCT apparatus, combines the images with an already combined image, and generates a combined image. The generation unit 705 outputs the generated image to a calculation unit 706 and an output unit 709 while storing the generated image in an internal memory. Then, the generation unit 705 acquires an image from the storage unit 704 again, and performs the image generation. As described above, the generation unit 705 performs the sequential generation processing.

If a control unit 708 receives a determination result indicating that the quality of the combined image is within the predetermined range by a determination unit 707, instructs the OCT apparatus 701 not to permit to continue the image capturing. Simultaneously with the processing, or instead of the processing, the control unit 708 can stop storing the images generated by the OCT apparatus 701, transmitting the images to the image processing apparatus 702, or acquiring the images by the image processing apparatus 702, or can perform notification of completion of the examination to the subject.

By the processing, unnecessary imaging can be prevented and the burden of the subject in the imaging can be reduced. The processing according to the present exemplary embodiment is effective in a case where the processing of scanning the imaging region of the retina and forming the image is faster than the processing of generating the combined image and the calculation processing of the value indicating the image quality.

In addition to the above, the control unit 708 performs overall control of each unit in the image processing apparatus 702. The output unit 709 displays the combined image generated by the generation unit 705 on a display unit 710 as needed. By the processing, the tomographic image to be displayed on the display unit 710 is sequentially updated. Accordingly, the image to be displayed becomes a sharp image as time advances.

Figure 8:
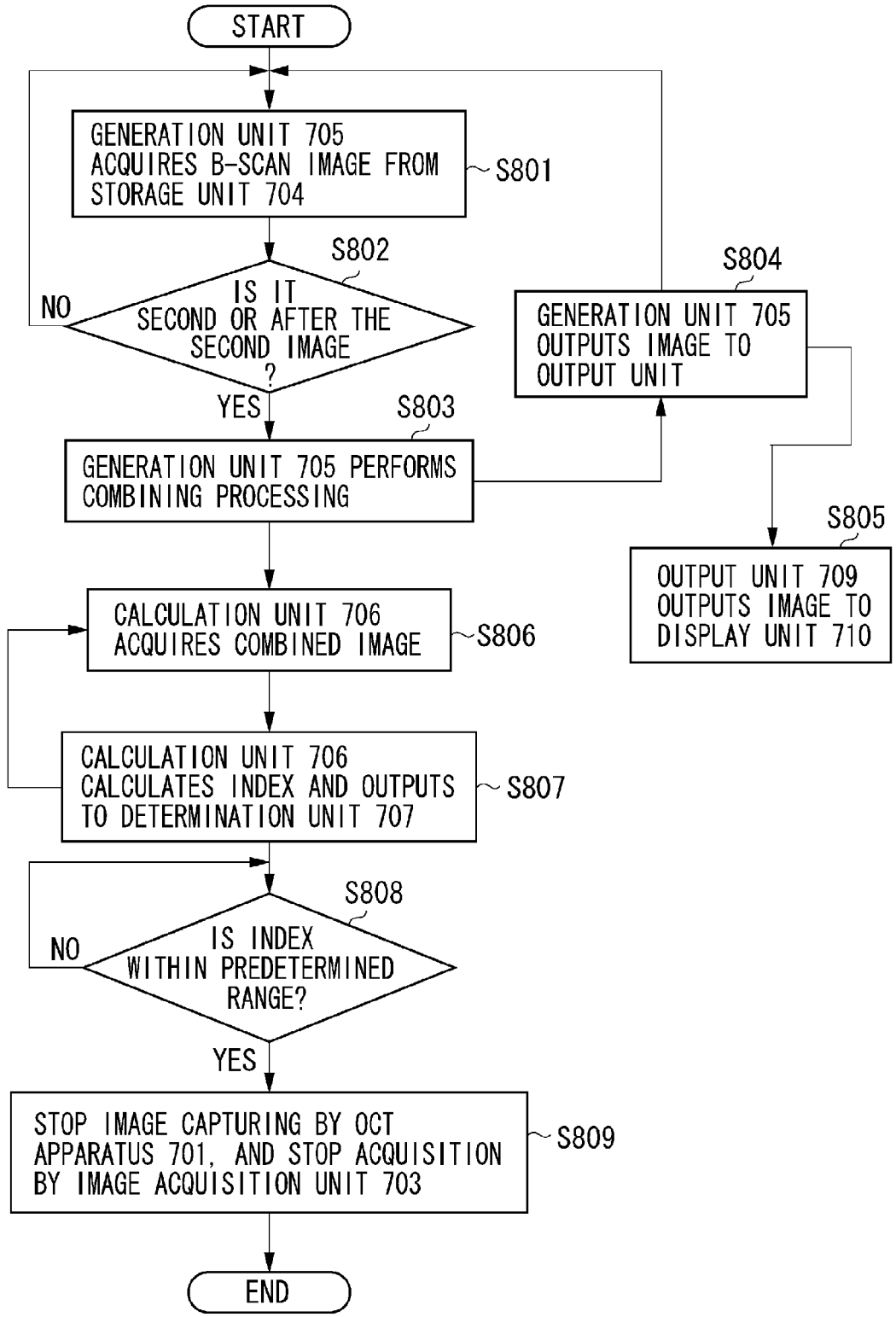
FIG. 8 is a flowchart illustrating the flow of processing performed by an image processing apparatus 702.

The flow of the processing in the image processing apparatus 702 according to the second exemplary embodiment is described with reference to the flowchart in FIG. 8. Descriptions overlapping with those in the first exemplary embodiment are omitted. The image acquisition unit 703 receives an image from the OCT apparatus 701 and stores the image in the storage unit 704. In the situation, in step S801, the generation unit 705 acquires one B-scan image from the storage unit 704.

In step S802, the control unit 708 determines whether the image acquired by the image acquisition unit 703 is a second image or an image after the second image. If the image is a first image (NO in step S802), the processing proceeds to step S801, and the generation unit 705 acquires the second B-scan image from the storage unit 704. If the image is the second B-scan image or after the second image (YES in step S802), in step S803, the control unit 708 inputs a plurality of images into the generation unit 705. Then, the generation unit 705 performs the processing for generating a combined image.

In step S804, the generated combined image is output to the output unit 709. In step S805, the display unit 710 displays the combined image. After the generation unit 705 output the combined image to the output unit in step S804, the generation unit 705 acquires a B-scan image from the storage unit 704 again. By the above-described processing, the generation unit 705 sequentially generates the combined images, and updates the combined image stored in the internal memory.

In step S806, the calculation unit 706 acquires the combined image. In step S807, the calculation unit 706 calculates an index indicating the image quality from the image. The calculation unit 706 outputs the value indicating the image quality to a determination unit 707 while sequentially performing the acquisition of the combined image and the calculation of the index value.

In step S808, the determination unit 707 determines whether the received index is within the predetermined range. If it is determined that the index is within the range (YES in step S808), the control unit 708 receives information about the determination. In step S809, the control unit 708 stops the acquisition of the image by the image acquisition unit 703 while transmitting an instruction not permitting, or stopping the image capturing by the OCT apparatus 701.

By the processing, the combination processing by the generation unit 705, the index calculation processing by the calculation unit 706, and the determination processing by the determination unit 707 is stopped while the updating processing of the B-scan image output by the output unit 709 and displayed by the display unit 710 is stopped.

As described above, the control unit 708 stops image capturing by the OCT apparatus 701 according to the image quality of the combined image. Accordingly, a tomographic image having the image quality necessary for diagnosis can be obtained while unnecessary imaging is stopped. Moreover, in each acquisition of the B-scan image with the progress of the image capturing, a combined B-scan image at the time is displayed. Accordingly, the operator of the imaging apparatus can visually check the image.

EXAMPLE 3

In a third exemplary embodiment, in order to shorten the time of the processing of generating a combined image by performing addition-average processing on a plurality of images, image information in the depth direction of a retina is reduced, and the processing of aligning the plurality of tomographic images is speeded up.

With respect to configurations of the system and the apparatus, descriptions of components similar to those in the first or second exemplary embodiment are omitted. Moreover, for the sake of simplicity, the description will be made based on the system configuration according to the first exemplary embodiment. However, the third exemplary embodiment can be applied to the system according to the second exemplary embodiment.

In the alignment unit 202 in the generation unit 104, when an overlap processing unit 2 performs alignment processing, the overlap processing unit 2 does not use all of pixels of an input tomographic image, but performs the processing in a form the tomographic image is substantially decreased in size. For example, as illustrated in FIG. 9, if the original B-scan image is H pixels long and W pixels wide, in the alignment processing, the B-scan image having smaller size of H2 pixels long and W2 pixels wide is used.

The length H2 and the width W2 can be any values as long as the accuracy of the alignment can be ensured. However, in the tomographic images of a retina, since the retina has a structure in which layers are overlapping in a direction perpendicular to the depth direction, information effective for the alignment is poor in a horizontal direction to the depth direction of the retina. Even if the number of the processing target pixels in the perpendicular direction is reduced, characteristics of the image are sufficient. Accordingly, problems in the alignment are few, and the reduction contributes to increase of the processing speed, and the reduction is preferable. In the example in FIG. 9, the width is defined as W=W2, and the pixels are thinned so that the height is to be H2<H.

Figure 9:
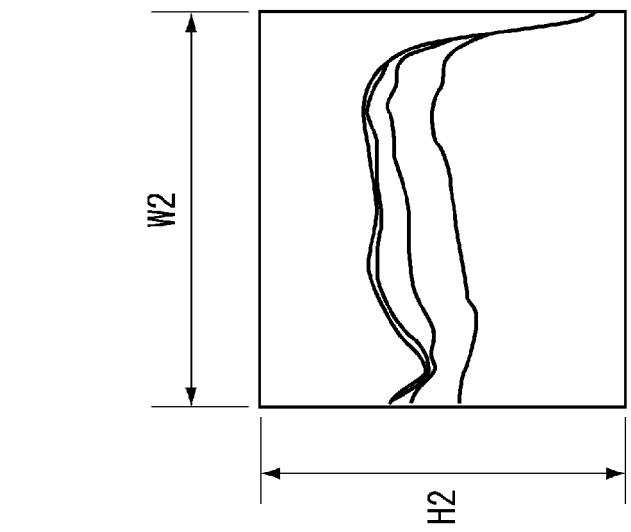
FIG. 9 illustrates a template region used for alignment processing performed by an alignment unit 202.
Figure 9:
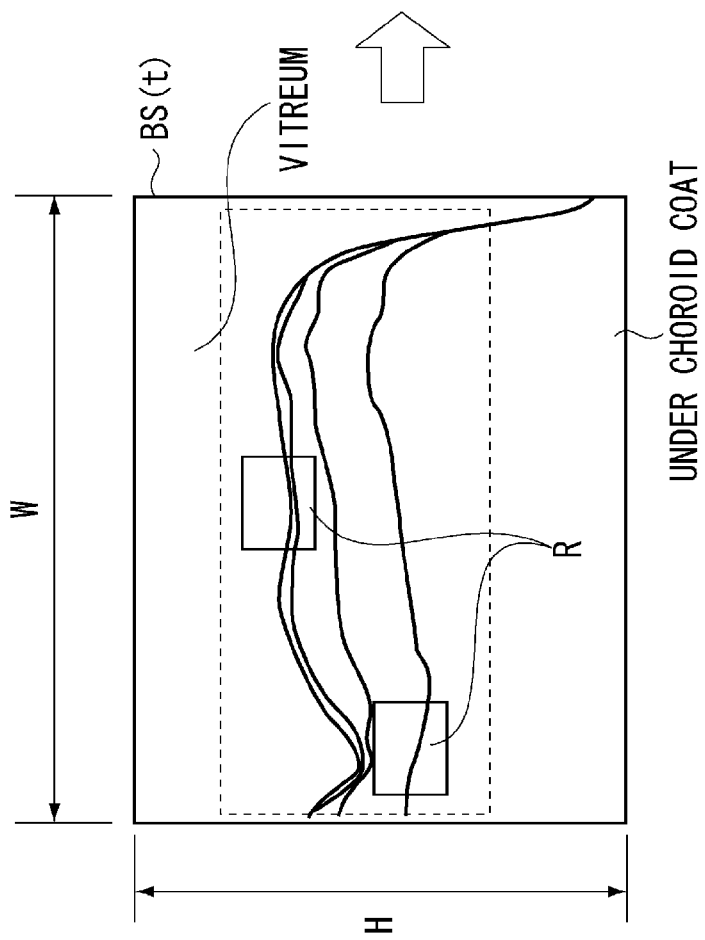

Alternatively, a region to be used for template matching in the alignment can be limited to a part of the B-scan image as illustrated in FIG. 9 by the dashed line to substantially reduce the number of the processing target pixels. Especially, in the tomographic image of the retina, as illustrated in FIG. 9, in a part corresponding to under the vitreum or the choroid coat, there is few signals. Accordingly, information effective for the alignment is poor, and if the information is not used for the alignment, the accuracy is not affected. On the contrary, it contributes to reduction of the processing time.

As described above, by binarizing the B-scan image in advance, extracting the region in the position deeper than the vitreum, and performing the template matching using only the region, extra processing can be reduced and the processing speed can be increased. Moreover, even if a region other than the region lower than the choroid coat is to be extracted, a region (deeper position viewed from an anterior eye) in a side lower than the vitreum and the region (shallower position viewed from the anterior eye) in a side upper than the choroid coat can be extracted. In such a case, the alignment unit 202 is provided with a layer extraction unit. The layer extraction unit extracts the region to be used for the template matching.

To the first exemplary embodiment, by applying the alignment processing that is the feature of the present exemplary embodiment, the intervals of the image capturing instructions can be reduced. Accordingly, the imaging time can be reduced. Moreover, to the second exemplary embodiment, by applying the alignment processing that is the feature of the exemplary embodiment, the intervals of the generation of the combined images that takes time can be reduced, and the intervals of the image quality determination can be reduced. Accordingly, unnecessary imaging can be prevented.

EXAMPLE 4

In a fourth exemplary embodiment, the values indicating the image quality are combined and used. With respect to configurations of the system and the apparatus, descriptions of components similar to those in the first or second exemplary embodiment are omitted. Moreover, for the sake of simplicity, the description will be made based on the system configuration according to the first exemplary embodiment. However, the fourth exemplary embodiment can be applied to the system according to the second exemplary embodiment.

The calculation unit 105 calculates an index indicating sharpness of an image together with the S/N ratio indicating the size of noise components described in the first exemplary embodiment. As the sharpness, a gradient is calculated in each boundary region in a retina layer in a tomographic image and an amount of statistics such as an average value, a maximum value, or the like of the values can be used.

In a B-scan image in the retina layer, as illustrated in FIG. 9, the layer structure is expressed in a form extending in the horizontal direction. Then, a blur due to an error in the overlapping processing is expressed in the vertical direction. In order to analyze an edge in the direction, as illustrated by R in FIG. 9, in the vicinity of the boundaries between the retina layers and the vitreum or the choroid coat, the gradient of the pixel values in the vertical direction can be calculated.

As the number of overlapping sheets increases, the S/N ratio of the overlapped B-scan image increases. On the other hand, due to remaining alignment errors, the boundary areas of the layer structure are blurred, and the sharpness decreases. As described above, the use of the gradient and the evaluation of the sharpness provides the index for preventing the increase of the blurs.

As a value indicating the size of the noise component, various index values can be employed. In the OCT, the size of the noise component contained in the tomographic image is dominant to the image quality. Accordingly, for example, in a histogram of the image, the calculation unit 105 can calculate a distance between a peak of the strength of the signal component and a peak of the strength of the noise component.

As another index, a numerical value that varies depending on a distribution profile of the histogram of the overlapped B-scan image can be used. For such a numerical value, the degree of distortion K illustrated in the following mathematical expression (3) can be used.

[Math.1]

$$K = \Sigma(k-m)^3 \cdot P(k)/\sigma^3 \qquad \text{mathematical expression (3)}$$

wherein P(k) is a value of a k-th component in the histogram, and expresses the frequency of a pixel whose pixel value is k, and m is a pixel average value. The degree of distortion K is an amount of characteristic whose value increases as the histogram becomes asymmetric.

Figure 10A:
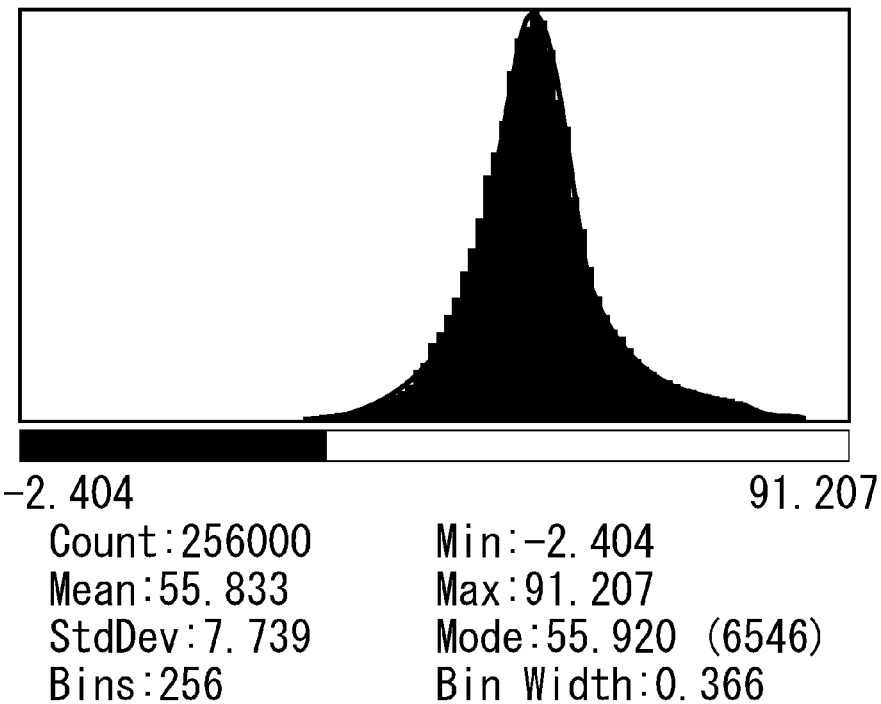
FIG. 10A illustrates a degree of distortion calculated as a value indicating image quality.

As described above, in the OCT tomographic image, noise components are dominant, and a histogram of a B-scan image that is not overlapping-processed has a shape nearly symmetric as illustrated in FIG. 10A. However, the noise components are random, and by performing the overlapping processing, the noise components are canceled. Then, components corresponding to signals of the subject become relatively strong.

Figure 10B:
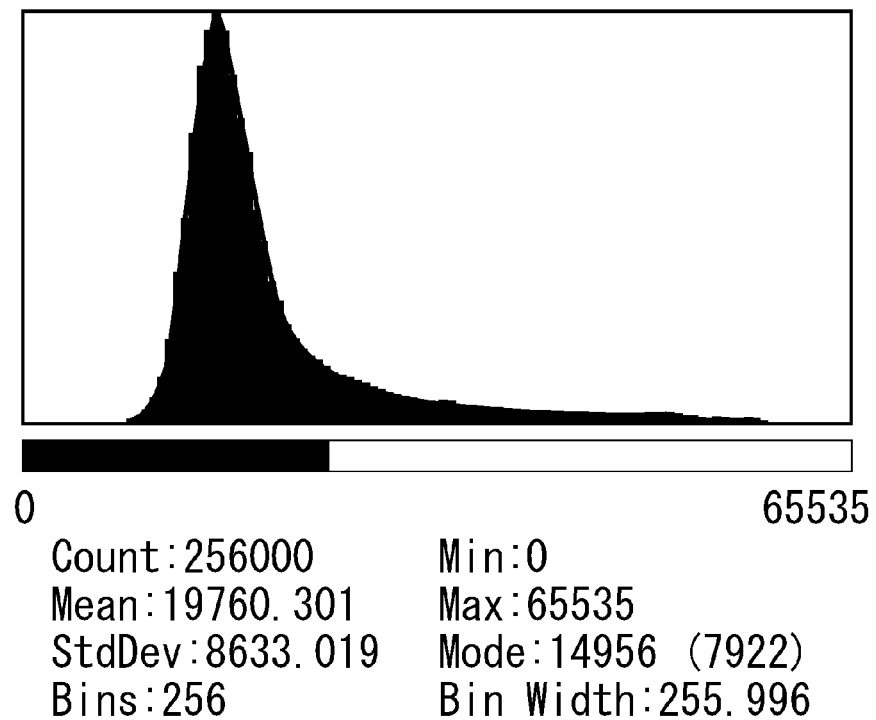
FIG. 10B illustrates a degree of distortion calculated as a value indicating image quality.
Figure 10C:
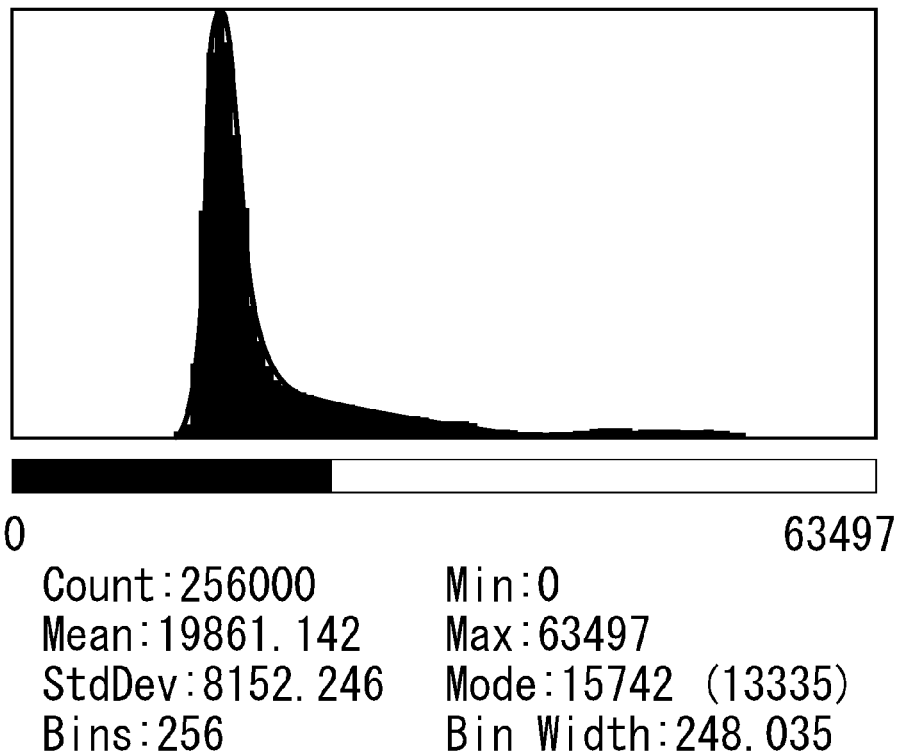
FIG. 10C illustrates a degree of distortion calculated as a value indicating image quality.

In a B-scan image of a fundus, retina layers are expressed. However, in the image, the layers have different pixel value levels. Accordingly, the distribution profile of the pixel values is not symmetric. Accordingly, as a result of the overlapping processing, the noise components are canceled, and the shape of the histogram becomes asymmetric. FIG. 10B and FIG. 10C illustrate cases where the number of overlapping sheets is 5 and 30 respectively. As the number of overlapping sheets increases, the distribution profiles become asymmetric.

Figure 11A:
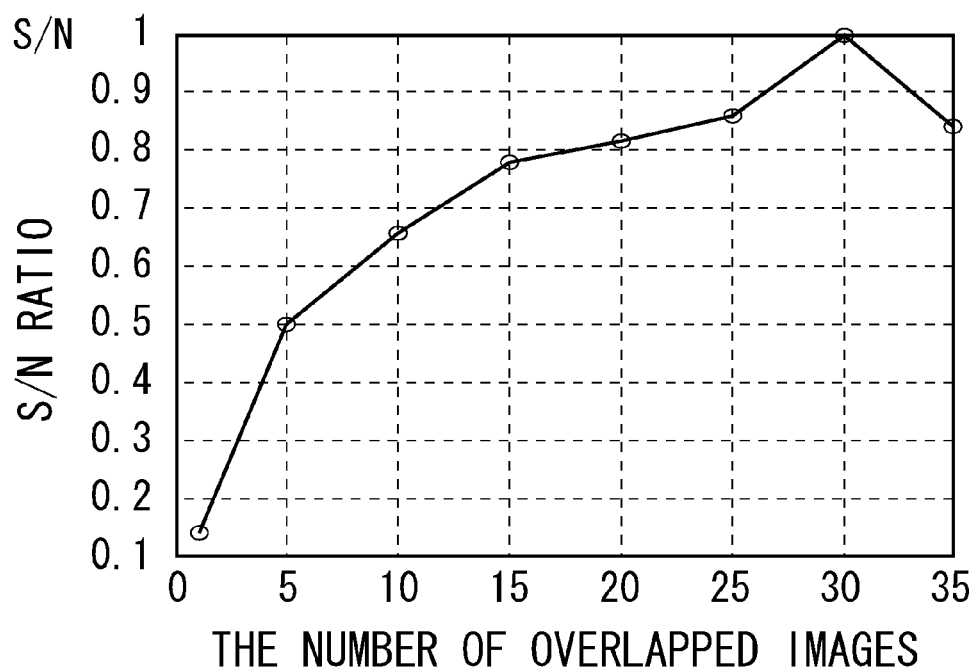
FIG. 11A is a graph illustrating a relationship between the number of images to be combined and a value indicating image quality of combined images.
Figure 11B:
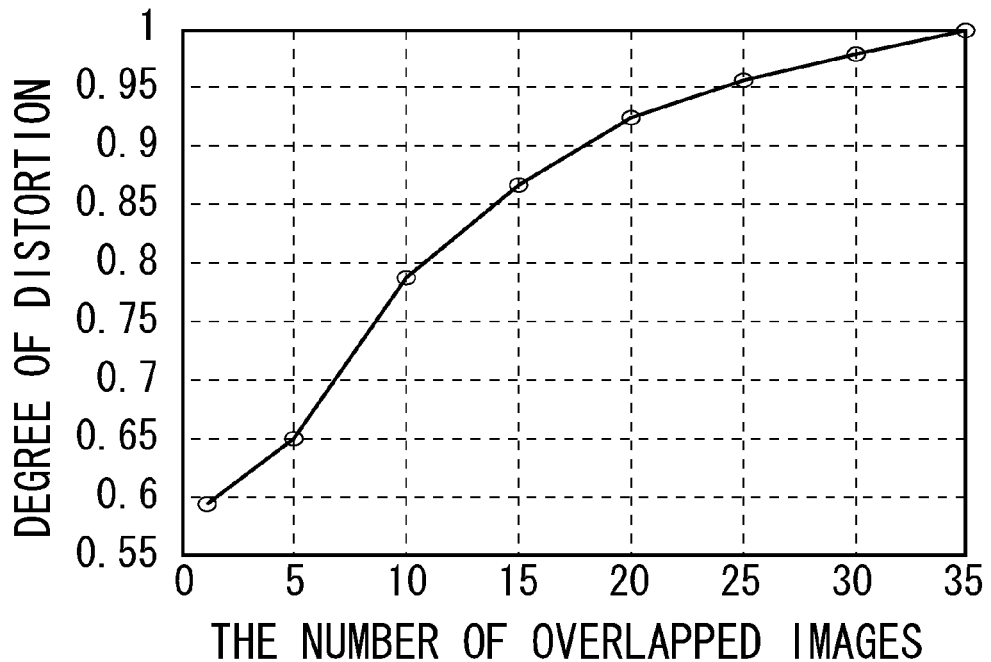
FIG. 11B is a graph illustrating a relationship between the number of images to be combined and a value indicating image quality of combined images.
Figure 11C:
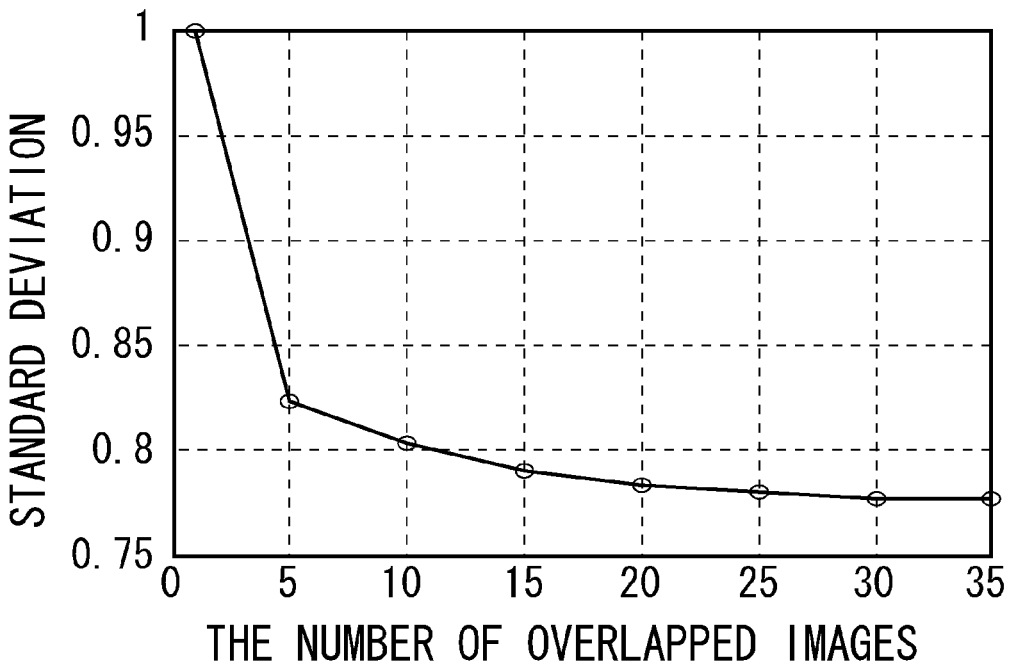
FIG. 11C is a graph illustrating a relationship between the number of images to be combined and a value indicating image quality of combined images.

FIGS. 11A, 11B, and 11C illustrate relationships between the index described in step S400 and the number of overlapping sheets. FIG. 11A illustrates the S/N ratios, FIG. 11B illustrates the degrees of distortion of a histogram, and FIG. 11C illustrates the standard deviations.

If the S/N ratio is used for the image quality index, even if the number of overlapping sheets exceeds 20, the image quality is not so much improved. Accordingly, for example, when the S/N ratio exceeds 0.8, the image capturing is stopped. In the case of the degree of distortion in the histogram, similarly, a threshold is set in advance. When the degree of distortion exceeds the threshold, the image capturing is stopped.

On the other hand, the standard deviation corresponds to the amount of noise. Accordingly, when the amount of noise becomes lower than a threshold, the image capturing is stopped. These thresholds are determined in advance by calculating relationships between the image quality and the index necessary for diagnosis by a vision assessment test, or the like, and stored in the storage unit 108 before image capturing.

Moreover, graph information indicating such a corresponding relationship between the number of the images to be combined and values indicating the image quality of the images can be stored in the storage unit 108, and images of the number at which the gradient of the graph becomes less than a predetermined threshold can be captured.

Due to characteristics of the subject or the other shooting conditions, noise per image may vary for each imaging target. To cope with such a case, the relationship information illustrated in FIGS. 11A, 11B, and 11C can be stored in the storage unit 108, and an appropriate number of overlapping sheets can be set according to the image quality of the first image. In such a case, image capturing of the set number of sheets is to be performed.

Moreover, in the first exemplary embodiment, the determination unit 106 can store history information of input values indicating image quality. At the time when the degree of improvement of the image quality becomes less than a predetermined threshold, the imaging instruction can be stopped and the image can be output.

In such a case, in the second exemplary embodiment, the control unit 708 can perform control for stopping image capturing to the OCT apparatus 701. By the processing, if the image quality is not so much improved even if addition processing is performed on the image, the image capturing is stopped at the time. Accordingly, unnecessary imaging is stopped and burden in the imaging can be reduced.

EXAMPLE 5

In a fifth exemplary embodiment, the present invention is applied to a so-called multibeam OCT apparatus that can simultaneously scan different regions on a retina with a plurality of measurement lights. The present invention can also be applied to an OCT that has a plurality of measurement lights. In the exemplary embodiment, an example of application of the present invention to an ophthalmologic photographing apparatus that can capture an image in a wide area at a high speed is described.

Figure 12:
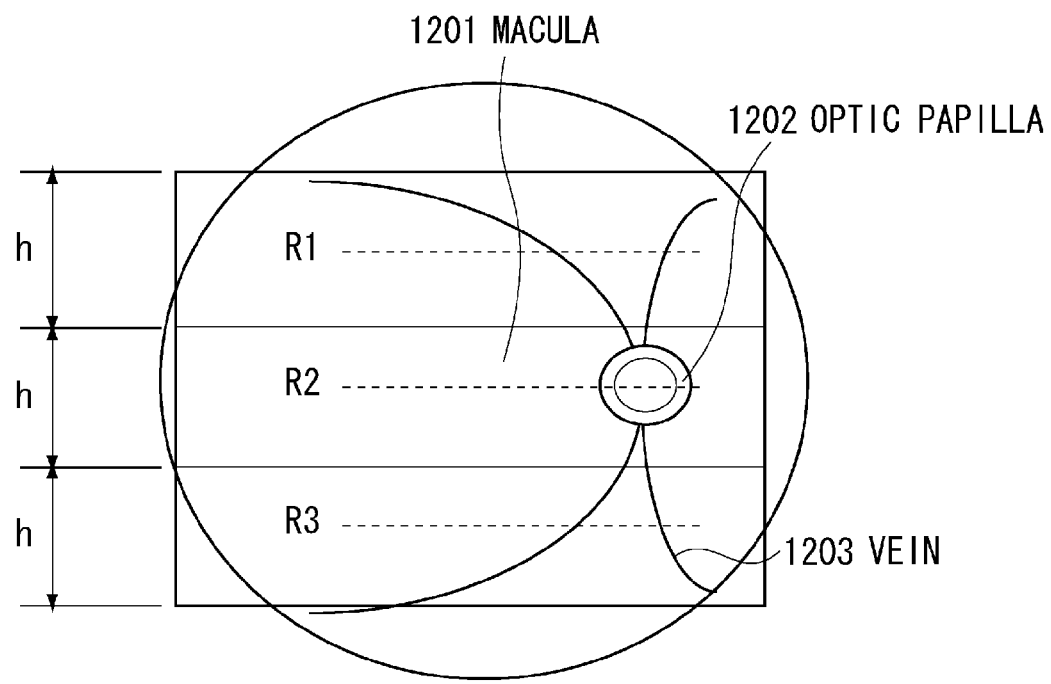
FIG. 12 illustrates regions of a retina scanned by each light flux of measurement lights in a multi-beam type OCT apparatus.

In the present exemplary embodiment, as illustrated in FIG. 12, a tomographic image acquisition unit 1 simultaneously emits light flux of independent measurement lights to regions having heights h of R1, R2, and R3 respectively to the depth direction, which are formed by dividing an imaging range into three, and captures images. In each region, the broken line illustrates a position for B-scan to be an overlapping target. Partial images obtained by the B-scan in the three positions can be simultaneously acquired. The regions scanned by each measurement light may be partially overlapped.

In FIG. 12, the image acquisition unit 103 scans each region illustrated by the broken lines a plurality of times, and acquires partial images corresponding to each region. The acquisition can be performed in the three positions simultaneously or sequentially. In a case where the target is a fundus retina, there is an effect due to eye movement. Accordingly, it is preferable to acquire the images in a short period of time as much as possible, and the acquisition is simultaneously performed. The acquired partial images at three positions are output to the generation unit 104.

The generation unit 104 performs alignment processing on the input partial images in each region separately for each region, performs addition-average processing, generates partial images, and outputs the images to the calculation unit 105.

The calculation unit 105 calculates indexes indicating image quality for each of the three overlapped partial images. The indexes to be calculated can be any of the indexes in the above-described exemplary embodiments. For example, if the degree of distortion of a histogram is used, the calculation unit 105 calculates three degrees of distortion of K1, K2, and K3 for each overlapped B-scan image, and outputs the values to the determination unit 106.

By performing the alignment for each image corresponding to each measurement light and calculating the index values, it is not necessary to perform processing for aligning the three images. Accordingly, the imaging time can be shortened.

The generation unit 104 can perform the image combining processing after performing the alignment of the input three B-scan images, and calculate the indexes. In such a case, as illustrated in FIG. 12, a characteristic structure such as a macula 1201 or an optic papilla 1202 can be used for the alignment by the alignment unit 202, and a sharper image can be obtained.

The determination unit 106 determines whether to stop the tomographic image acquisition based on the input three values of the degrees of distortion. For example, all of the three degrees of distortion exceed a threshold as described in the above exemplary embodiments, and differences between the three degrees of distortion are at a level having no problem in the image quality, the image capturing operation is stopped.

Whether to permit the image capturing can be controlled only by the fact that the differences are less than the threshold. As described above, in the case where the tomographic image acquisition is performed separately in the plurality of regions, by performing the control so that each region exceeds the predetermined level, and the differences between the regions become small, the image quality can be maintained in all imaging regions.

According to the above-described exemplary embodiment, the image capturing instruction is issued according to the image quality as needed, the addition-average processing is performed on the captured images, and a new tomographic image is generated. Accordingly, unnecessary burden of the subject in the imaging can be reduced and the images of the desired image quality can be obtained.

Moreover, the addition-average processed images are sequentially generated and at the time when the image quality becomes within the predetermined range, the image capturing can be stopped. Accordingly, unnecessary burden of the subject in the imaging can be reduced and the images of the desired image quality can be obtained In the above-described exemplary embodiments, the B-scan images are used in the alignment processing and the combination processing. However, it is not limited thereto, the processing can be performed by A-scan image unit or by three-dimensional tomographic image unit.

Moreover, in the image capturing instruction by the control unit 107 in the first exemplary embodiment, it is possible to issue the instruction for capturing a plurality of tomographic images at a time. Moreover, while the number of combined images from the start of the processing according to the exemplary embodiments of the present invention is small, the amount of noise in the combined images is large. Accordingly, the instruction for capturing many tomographic images can be issued at a time, and as the combining processing proceeds, the number of images to be captured can be reduced. In such a case, the number of times of the combining processing, the index calculation processing, the determination processing, and the like can be reduced.

The generation unit 104 adds a newly captured image to a combined image and performs the combining processing. However, the combined image can be generated by sequentially combining the captured images without using the already combined image.

The functions of the OCT apparatus and the image processing apparatus in the optical coherence tomography system according to the above-described exemplary embodiments can be mounted as one optical coherence tomography apparatus.

Moreover, the functions of the image processing apparatus 102 can be implemented by cooperatively working software and hardware. In such a case, in the control unit 107 including a central processing unit (CPU), a read-only memory (ROM), and a random access memory (RAM), the CPU loads a program for implementing the flow of the processing stored in the ROM into the RAM, and the CPU sequentially executes the instructions described in the program. By the operation, the hardware and the software in the electronic computer work cooperatively, and then, the present invention is realized. Further, only a part of the present invention can be realized by the software and the hardware by cooperatively working.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-045544 filed Mar. 2, 2010 and No. 2011-002089 filed Jan. 7, 2011, which are hereby incorporated by reference herein in their entirety.

REFERENCE SIGNS LIST

100: optical coherence tomography system
101: OCT apparatus
102: image processing apparatus
104: generation unit
105: calculation unit
106: determination unit
107: control unit

The invention claimed is:

1. An image processing apparatus comprising:
a generation unit configured to generate a combined tomographic image by combining tomographic images for a designated position in an imaging target captured by an optical coherence tomography apparatus;
a determination unit configured to determine whether image quality of the combined tomographic image is within a predetermined range; and
a control unit configured to control the optical coherence tomography apparatus whether to permit the image capturing for the designated position in response to a determination by the determination unit.

2. The image processing apparatus according to claim 1, wherein the control unit controls the optical coherence tomography apparatus to capture a tomographic image for the designated position if the determination unit determines that the image quality is out of the predetermined range.

3. The image processing apparatus according to claim 2, wherein the generation unit combines the combined tomographic image whose image quality is determined by the determination unit with the tomographic image obtained according to the permission of image capturing by the control unit.

4. The image processing apparatus according to claim 1, wherein the control unit controls the optical coherence tomography apparatus not to permit image capturing of the designated position if the determination unit determines that the image quality is within the predetermined range.

5. The image processing apparatus according to claim 1, wherein the control unit controls the optical coherence tomography apparatus to repeatedly capture images of the designated position, and the generation unit to combine the captured tomographic images, and if the determination unit determines that image quality of the new tomographic image obtained by the combining processing is within the predetermined range, controls the optical coherence tomography apparatus not to permit continuing the image capturing.

6. The image processing apparatus according to claim 1, wherein the generation unit includes an alignment unit for aligning the combined tomographic image and the tomographic image, which are targets of the combining processing.

7. The image processing apparatus according to claim 6, wherein the generation unit combines the combined tomographic image and the tomographic image by increasing a weight of the tomographic image as positional deviation of the tomographic image becomes small, as a result of the alignment.

8. The image processing apparatus according to claim 6, further comprising an extraction unit for extracting at least one of a region lower than a vitreum and a region upper than a choroid coat from the tomographic image if the imaging target is a retina,
wherein the alignment unit performs alignment using a tomographic image in the extracted region.

9. The image processing apparatus according to claim 1, further comprising a calculation unit configured to calculate a value indicating quality of the combined tomographic image obtained by the generation unit.

10. The image processing apparatus according to claim 9, wherein the calculation unit calculates a value indicating noise and a value indicating sharpness of the combined tomographic image, and
wherein the determination unit determines whether each of the value indicating the noise and the value indicating the sharpness is within the predetermined range respectively.

11. The image processing apparatus according to claim 9, wherein the calculation unit calculates a distance between a position of a peak of noise components and a position of a peak of signal components in a histogram of a tomographic image as a value indicating the image quality of the combined tomographic image.

12. The image processing apparatus according to claim 9, wherein the calculation unit calculates degree of distortion of a histogram of a tomographic image as a value indicating the image quality of the combined tomographic image.

13. The image processing apparatus according to claim 1,
wherein the optical coherence tomography apparatus simultaneously emits light flux of a plurality of measurement lights to an imaging target and generates a tomographic image based on returned light from the imaging target of the emitted measurement light, and
wherein the determination unit determines whether a difference between values indicating image quality calculated for each partial image corresponding to each light flux of the measurement lights is within a predetermined range.

14. The image processing apparatus according to claim 1,
wherein the optical coherence tomography apparatus simultaneously emits light flux of a plurality of measurement lights to an imaging target and generates a tomographic image based on returned lights from the imaging target of the emitted measurement lights, and wherein the determination unit determines whether a value indicating image quality is within a predetermined range with respect to a tomographic image formed by aligning and combining each of partial images corresponding to each of the measurement lights.

15. The image processing apparatus according to claim 1,
wherein the optical coherence tomography apparatus repeatedly captures an image in a designated position in an imaging target and sequentially forms a tomographic image, and wherein the generation unit acquires the formed tomographic image in parallel with the image capturing by the optical coherence tomography apparatus, and combines the tomographic image with an already combined tomographic image to sequentially generate a new combined tomographic image,
and the image processing apparatus further comprising:
a control unit configured to control the optical coherence tomography apparatus to stop the image capturing if the calculated image quality becomes within a predetermined range.

16. A control method of an optical coherence tomography apparatus, comprising the steps of:

generating a combined tomographic image by combining tomographic images in a designated position in an imaging target captured by an optical coherence tomography apparatus;

determining whether image quality of the combined tomographic image is within a predetermined range;

controlling whether to permit the optical coherence tomography apparatus to capture an image in the designated position according to a determination by the determination step that the image quality is out of the predetermined range; and generating a new combined tomographic image by combining the combined tomographic image with the tomographic image of the designated position obtained in the control step.

17. The control method of an optical coherence tomography apparatus according to claim 16, further comprising the step of:

calculating a value indicating quality of the combined tomographic image obtained in the generation step.

18. An optical coherence tomography system comprising:

a light source configured to emit low-coherence light;

an interference light generation unit configured to split the light emitted from the light source into measurement light traveling toward an imaging target and reference light traveling toward a reference object, and generate interference light of the measurement light obtained via the imaging target and the reference light obtained via the reference object;

a scanning optical system configured to scan the imaging target by sequentially changing incident positions of the measurement light in the imaging target;

an image forming unit configured to form a tomographic image of the scanned imaging target based on the interference light generated by the interference light generation unit;

a generation unit configured to generate a combined tomographic image by combining the tomographic images formed by the image forming unit;

a determination unit configured to determine whether image quality of the combined tomographic image is within a predetermined range;

a control unit configured to control the light source, the scanning optical system, and the image forming unit to perform control whether to permit the image capturing according to a determination by the determination unit that the image quality is out of the predetermined range, wherein the generation unit generates a new combined tomographic image by combining the combined tomographic image and the tomographic image obtained according to the control by the control unit.

19. The optical coherence tomography system according to claim 18, further comprising a calculation unit configured to calculate a value indicating quality of the combined tomographic image obtained by the generation unit.

20. An image processing method, comprising the steps of:

generating a combined tomographic image by combining tomographic images in a designated position in an imaging target captured by an optical coherence tomography apparatus;

determining whether image quality of the combined tomographic image is within a predetermined range; and generating a new combined tomographic image by combining the combined tomographic image with a tomographic image according to a determination in the determination step that the image quality is out of the predetermined range, the tomographic image being obtained in the designated position by the optical coherence tomography apparatus.

21. An image processing apparatus comprising:

a generation unit configured to generate a combined tomographic image by combining tomographic images in a designated position in an imaging target captured by an optical coherence tomography device;

a determination unit configured to determine whether image quality of the combined tomographic image is within a predetermined range; and a generation unit configured to generate a new combined tomographic image by combining the combined tomographic image with a tomographic image according to a determination by the determination unit that the image quality is out of the predetermined range, the tomographic image being obtained in the designated position by the optical coherence tomography device.

22. The image processing apparatus according to claim 21, wherein the generation unit includes an alignment unit for aligning the combined tomographic image and the tomographic image, which are targets of the combining processing.

23. The image processing apparatus according to claim 22, further comprising an extraction unit configured to extract at least one of a region lower than a vitreum and a region upper than a choroid coat from the tomographic image if the imaging target is a retina, wherein the alignment unit performs alignment using a tomographic image in the extracted region.

24. The image processing apparatus according to claim 21, further comprising a calculation unit configured to calculate a value indicating quality of the combined tomographic image obtained by the generation unit.

25. The image processing apparatus according to claim 24, wherein the value is a signal-to-noise (S/N) ratio in the combined tomographic image.

26. The image processing apparatus according to claim 21, further comprising a display control unit configured to display the combined tomographic image on a display unit.

* * * * *